United States Patent [19]

Chen

[11] Patent Number: 5,655,947

[45] Date of Patent: Aug. 12, 1997

[54] ULTRA-SOFT, ULTRA-ELASTIC GEL AIRFOILS

[75] Inventor: John Youngfu Chen, Pacifica, Calif.

[73] Assignee: Applied Elastomerics, Inc., South San Francisco, Calif.

[21] Appl. No.: 705,096

[22] Filed: May 23, 1991

Related U.S. Application Data

[63] Continuation-in-part of Ser. No. 527,058, May 21, 1990, which is a continuation-in-part of Ser. No. 211,426, Jun. 24, 1988, which is a continuation-in-part of Ser. No. 921,752, Oct. 21, 1986, abandoned, which is a continuation-in-part of Ser. No. 572,172, Jan. 18, 1984, Pat. No. 4,618,213, which is a continuation-in-part of Ser. No. 458,703, Jan. 17, 1983, abandoned, which is a continuation-in-part of Ser. No. 134,977, Mar. 28, 1980, Pat. No. 4,369,284, which is a continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^6$ ........................................ A63H 27/00
[52] U.S. Cl. ........................ 446/46; 446/491; 446/34
[58] Field of Search ........................ 446/46–48, 486, 446/491, 34; 273/424, 425, 428, 58 A

[56] References Cited

U.S. PATENT DOCUMENTS

| | | | |
|---|---|---|---|
| 2,454,598 | 11/1948 | Doyle | 446/66 |
| 3,594,945 | 7/1971 | Turney | 446/48 |
| 3,653,151 | 4/1972 | Laurent | 471/66 |
| 3,676,387 | 7/1972 | Lindlof | 260/285 B |
| 4,104,822 | 8/1978 | Rodgers | 446/48 |
| 4,369,284 | 1/1983 | Chen | 524/476 |
| 4,466,212 | 8/1984 | Lehman | 446/46 |
| 4,516,946 | 5/1985 | Rodarte | 446/46 |
| 4,516,947 | 5/1985 | Pircher | 446/46 |
| 4,560,358 | 12/1985 | Adler | 446/46 |
| 4,618,213 | 10/1986 | Chen | 446/486 X |
| 4,669,995 | 6/1987 | Lombard | 446/48 |
| 4,669,996 | 6/1987 | Bershak | 446/48 |
| 4,681,553 | 7/1987 | Rodarte | 446/46 |
| 4,737,128 | 4/1988 | Moormann et al. | 446/46 |
| 4,820,230 | 4/1989 | Richards | 446/48 |
| 4,940,441 | 7/1990 | Novinsky | 446/46 |
| 4,944,363 | 7/1990 | Osher | 273/58 |
| 4,944,707 | 7/1990 | Silverylate | 446/48 |
| 4,957,465 | 9/1990 | Madhava | 446/66 |
| 5,026,054 | 6/1991 | Osher et al. | 273/58 A |

FOREIGN PATENT DOCUMENTS

1268431  3/1972  United Kingdom.

*Primary Examiner*—Mickey Yu

[57] ABSTRACT

A novel rotating aerodynamic toy in the form of a ultra-elastic gel airfoil which is suitable for launch in light or heavy wind conditions and capable of performing various aerodynamic effects including climb, stall, return, straight-line flight and other aerobatics. The ultra-elastic properties of the airfoil allow the airfoil to transform its aerodynamic profile at launch and while in flight.

28 Claims, 12 Drawing Sheets

Characteristic Flight Regions for Different Wind Speeds

STEP 1:
PLACE SOLID PRISMATOID CONTAINING MORE THAN ONE GEL REGION ON FLAT SUPPORTING SURFACE SO AS TO FORM A BASE WITH SAID SUPPORTING SURFACE AND MEASURE THE DIAMETER OF SAID BASE WITH A RULER OR MEASURING DEVICE.

STEP 2:
WITHOUT DISTRUBING SOLID PRISMATOID OF STEP 1, MEASURE THE DISTANCE OF PRISMATOID FROM ITS HIGHTEST POINT RESTING ON THE SUPPORT SURFACE TO THE SUPPORT SURFACE WITH A RULER OR MEASURING DEVICE.

STEP 3:
THE MEASURE OBTAINED IN STEP 1 IS THE BASE DIAMETER, D; AND THE MEASURE OBTAINED IN STEP 2 IS THE ALTITUDE, H.

ULTRA-SOFT, ULTRA-ELASTIC GEL AIRFOILS

RELATED APPLICATIONS AND PATENTS

This application is a continuation-in-part of application Ser. No. 527,058 filed May 21, 1990 which is a continuation-in-part of application Ser. No. 211,426 filed Jun. 24, 1988 which is a continuation-in-part of application Ser. No. 921,752 filed Oct. 21, 1986 now abandoned which is a continuation-in-part of application Ser. No. 572,172, filed 18 Jan. 1984 and issued as U.S. Pat. No. 4,618,213 on 21 Oct. 1986, which is a continuation-in-part of application Ser. No. 458,703, filed 17 Jan. 1983 now abandoned, which is a continuation-in-part of application Ser. No. 134,977, filed 28 Mar. 1980 and issued as U.S. Pat. No. 4,369,284 on 18 Jan. 1983, which in turn is a continuation-in-part of application Ser. No. 916,731, filed 19 Jun. 1978, now abandoned which is a continuation-in-part of application Ser. No. 815,315, filed 13 Jul. 1977, now abandoned which is a continuation-in-part of application Ser. No. 778,343, filed 17 Mar. 1977 now abandoned. The subject matter contained in the related applications and patents are specifically incorporated herein by reference.

FIELD OF THE INVENTION

The present invention relates to aerodynamic toys.

BACKGROUND OF THE INVENTION

There are various prior art aerodynamic toys (flyers) in the form of airfoils. The ability to safely launch and land such flyers is of major concern for everyone involved with safety. Flyers of rigid construction have been fitted with rubber bumpers. While some flyers are completely made of soft foam or sheet rubber. Others are inflatable or, in some instants, are substantially made of fabric.

In general, prior art flyers are designed to maintain a rigid or fixed configuration or shape (i.e. aerodynamic profile) during flight. The typical pocket flyers (i.e. made from fabric or rubber) are somewhat flexible and are much safer; they are also foldable. In flight, however, due to the rotation imparted to the flyer at launch (i.e. centrifugal force), these more flexible flyers also exhibit a substantially rigid or fixed aerodynamic profile characterized by a substantially fixed radii or shape The inflatable flyers of the prior art are designed with shape holding features which serve to maintain a predetermined or preselected aerodynamic profile. The rigid, fixed, build-in aerodynamic profiles which are characteristic of all prior art flyers determine the toy's ultimate aerodynamic characteristics and most importantly, their lift/drag characteristics. These flyers of the prior art (when launched) will substantially fly in a predetermined flight-path and at all times, subject to the mercy of the wind.

Most importantly, all prior art flyers are not well suited for flying in the wind. It is well known that the wind is not especially kind to such flyers and throwers must avoid anything more than a very light breeze. As a rule, if there is more than 2–5 mph of wind, it's too windy to safely throw any prior art flyer; it will simply be blown away in anything more than a very light breeze. Even the most advanced, high-tech flyer, if caught by a light wind, can become unpredictable!

SUMMARY OF THE INVENTION

I have unexpectedly discovered novel airfoils made from ultra-soft, ultra-elastic gels, which are capable of sustained flight and perform various aerodynamic effects such as climb, stall, return, and other flight aerobatics. The gel airfoils of the invention can be made of a uniform gel material or can have one or more (external and/or internal) regions formed from at least one gel having a gel rigidity of about 20 gram or less to about 800 gram Bloom. The instant airfoils are characteristically blunt bodies or essentially unstreamlined shapes. The airfoils of the invention can be launched and flown safely under extremely varying wind conditions of less than 0.5 mph to greater than 40 mph. The high Reynolds Number (flight performance) characteristics of the airfoils are attributed to their ultra-elastic properties which allows the (deformable) airfoils to transform its aerodynamic profile at launch and during flight. The transformation of the instant airfoils while in flight is unexpected. The airfoils of the invention comprises unstreamlined shaped blunt bodies. These blunt shapes are transformed by rotational forces during flight into substantially streamline airfoils exhibiting sustained lift.

Generally, the invention is useful as aerodynamic toys comprising: an ultra-elastic gel airfoil having a profile defining a camber, said airfoil having an upper surface and an lower surface, said airfoil can have one or more holes; one or more cavities; one or more slots; a rough or pattern surface; one or more different gel rigidity regions; one or more of a first internal and a second external gel rigidity regions, said first and second gel rigidity reigions having different gel rigidities, and said airfoil having a one or more axes, a base contact diameter, D, and a altitude, H, said D having a value at least about 20% to about 200% of one of its axes, and said altitude having a value of about 20% to 80% of one of its axes; wherein the values of D and H being measured when said gel airfoil is supported on a support surface; the gel airfoil can have a general prismatoid shape, such as an ellipsoid, a spheroid, an oblate spheroid, a prolate spheroid and the like; the upper surface or lower surface of the gel airfoil can be interlocked with a foam material; and the gel airfoil is capable of exhibiting an elongation of at least 50% caused by the centrifugal force of rotation.

Generally, the method of launching the gel airfoils of the invention comprises:

(a) gripping the edge of an airfoil made from an ultra-soft and ultra-elastic gel between the forefinger and the thumb of one hand, and (b) elongating said airfoil by launching the airfoil with sufficient rotational velocity so as to elongate said airfoil at least 50% or greater due to the centrifugal force of rotation.

The various aspects and advantages of the invention will become apparent to those skilled in the art upon consideration of the accompanying disclosure and the drawings.

DETAILED DESCRIPTION OF THE INVENTION

It is somewhat strange and wonderful to watch an airfoil of the invention (thrown into a moderate wind) take off and soar like an "eagle" to an incredible height, stall, then dive earthward like an eagle when attacking prey from above. It is even more strange to catch an airfoil of the invention! As it hits the palm of the hand, the impact gives the feeling of catching a small anesthetized Amazon frog falling from the sky!

The airfoils of the present invention are not limited to any particular aerodynamic profile (see FIGS. 1, 5, 6, 7, & 8), although certain profiles may have advantages over others such as for speed, distance, climb, stall, return, etc. The basic principles of aerodynamics and airfoil design can be utilized to assist in selecting and forming the unstreamlined blunt shapes and resulting rotating streamline profiles of the ultra-soft, ultra-elastic gel airfoils of the invention. For example, see *Shape and Flow*, by A. H. Shapiro, 1961, Doubleday & Company, Inc.; *Aerodynamics of Wings and Bodies*, by H. Ashley, at al, 1965, Dover Publications, Inc.; *Theory of Flight*, by R. Von Mises, 1959, Dover Publications, Inc.; *Aerodynamics Theory*, W. F. Durand, Editor, Volume I–VI, 1963, Peter Smith Publisher, Inc.; *Rotary-Wing Aerodynamics*, W. Z. Stepniewski, et al, Volume I & II, 1984, Dover Publications, Inc.; *Incompressible Aerodynamics*, B. Thwaites, Editor, 1960, Oxford Press; *Modern Developments in Fluid Dynamics*, S. Goldstein, Editor, Volume I & II, 1950, Oxford Press; *Hydrodynamics*, by Sir H. Lamb, 1945, Dover Publications, Inc.; *Fluid-Dynamic Lift*, by S. F. Hoerner, 1975, Published by Mrs. Liselotte A. Hoerner; and *Fluid-Dynamic Drag*, by S. F. Hoerner, 1958, Published by the Author; *Foundations of Aerodynamics*, by Kuethe, Arnold M., et al, 3rd Edition, John Wiley & Sons, 1976. The subject matter contained in these publications are specifically incorporated herein by reference.

Generally, any aerodynamic profile can be selected for use in the design of the airfoil of the invention provided the blunt profile selected gives the airfoil (when launched by hand) a sustained flight-time in air that is greater than the time required for the airfoil to fall the vertical distance to the ground in free-fall when released from the same launch height.

Figure 1A:
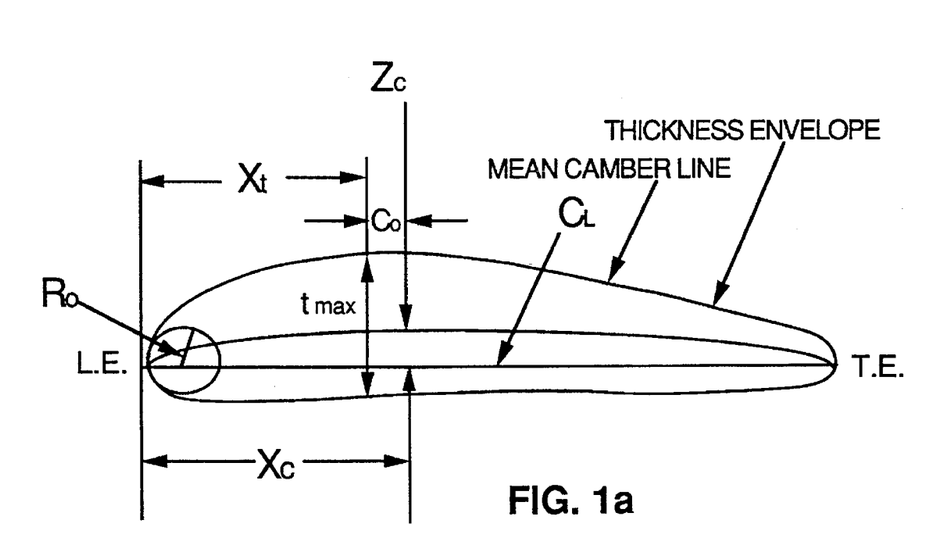
FIG. 1a. Representative static view of a spinning airfoil (at an elongation of at least 200%) showing various geometrical variables.
Figure 1B:
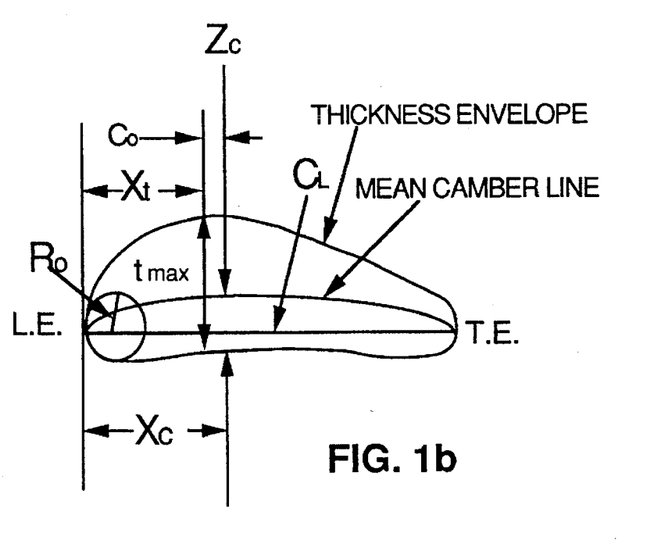
FIG. 1b. Representative normal view of the airfoil of FIG. 1a (at zero elongation) showing various geometrical variables.
Figure 2:
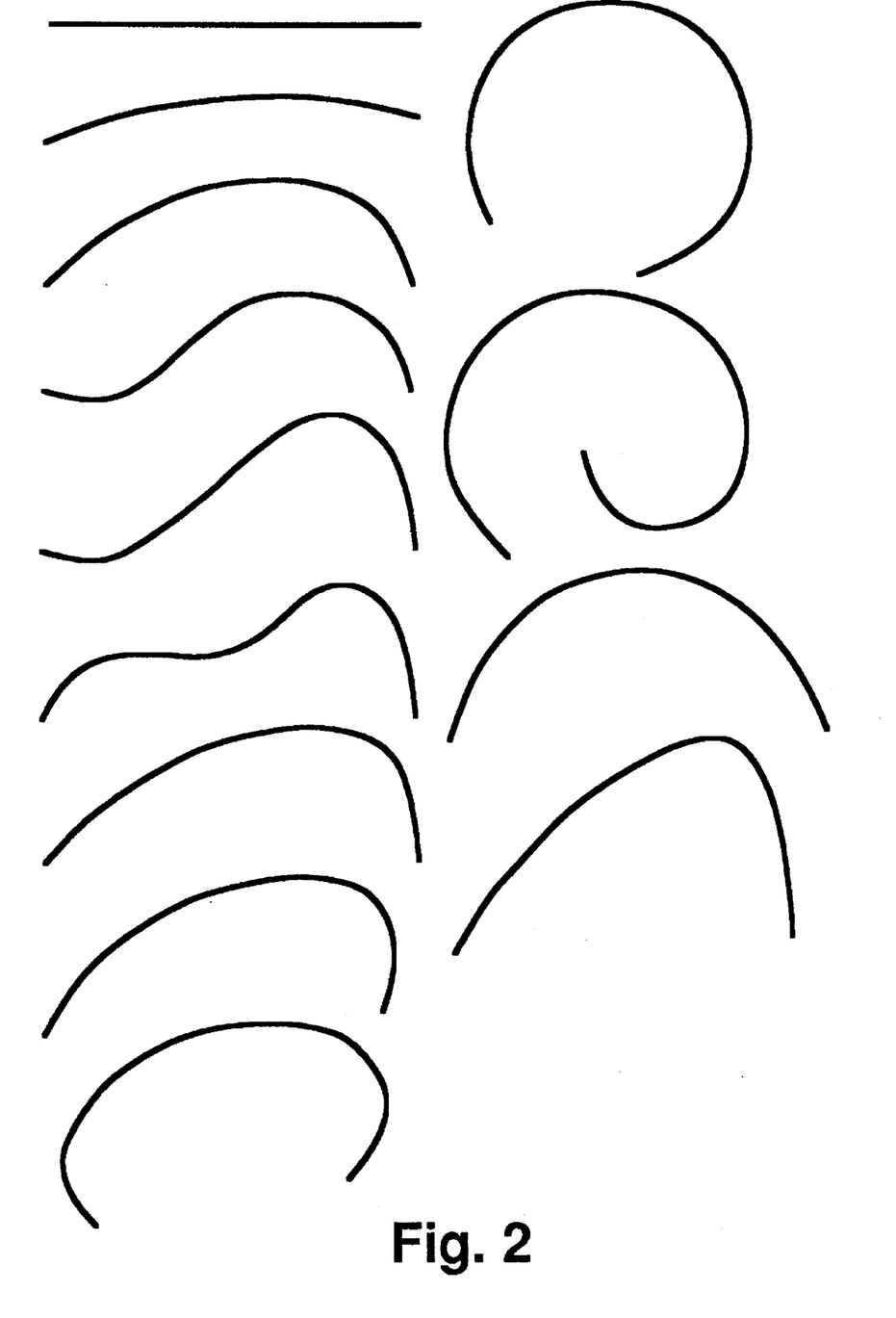
FIG. 2. Side view of selected examples of mean camber lines of airfoils of the invention.

The airfoils of the invention (in the spinning state) comprises a thickness envelope wrapped around a mean camber line as shown in FIG. 1. Aerodynamic spinning profiles for the airfoil of the invention can be selected with mean camber lines shown in FIG. 2 or any intermediate mean camber line. The mean camber line lies halfway between the upper and lower surfaces of the airfoil and intersects the chord line at the leading and trailing edges. An intermediate mean camber line can be obtained from any two adjacent mean camber lines shown in FIG. 2 by drawing a new intermediate mean camber line halfway between the adjacent mean camber lines. Likewise an intermediate mean camber line can be used together with another mean camber line or another intermediate mean camber line to derive a new intermediate mean camber line. The thickness envelope (bounded by an upper surface and a lower surface) of the airfoils of the invention can be of any suitable thickness provided the resulting airfoil is capable of sustained flight. Other geometrical variables of airfoils of invention are shown in FIG. 1; they include the cord line $C_L$; the maximum camber $Z_c$ of the mean camber line and its distance $X_c$ behind the leading edge; the maximum thickness $t_{max}$ and its distance $x_t$ behind the leading edge; the radius of curvature of the surface at the leading edge, $r_o$, and the angle between the upper and lower surfaces at the trailing edge. In the design of the airfoils of the invention, the geometrical variables should be selected so as to provide the instant airfoils with the ability for sustained flight in low as well as high wind conditions.

A suitable range for $C_L$ is lees than about 3 cm to about 30 cm or more. The value $(X_c-X_t)=C_o$ can range from less than about 2 cm to greater than about 20 cm. The variable $t_{max}$ can range from less than about 1 cm to greater than about 7 cm.

The aerodynamic profile (i.e. cross-sectional geometry) of the airfoils of the invention can be varied as desired. A helpful way of designing and/or viewing the airfoils' profile from the side is to vertically cut the airfoils into adjacent slices. For example, the adjacent slices can be a series of different cross sections (i.e. cross sections of different geometrical variable values). The airfoils of the invention can be designed with any desired profile cross section or varying profile cross sections provided such profiles will maintain sustained flight. An easy way to simulate the flight airfoil profile from the non-spinning static or blunt airfoil profile is by elongating the blunt airfoil profile approximate the elongation sustained in flight. Another method is to spin the blunt airfoil as discussed below.

Since the instant airfoils are three dimensional objects, they can be sliced to show more than one cross section. For example, viewing down on the upper surface, airfoils of the invention can have shapes such as a ring, circle, square, triangle, parallelogram, rhombus, trapezoid, quadrilateral, pentagon, hexagon, heptagon, octagon, nonagon, decagon, undecagon, dodecagon, polygon, sector, an ellipse, a parabola and the like. The general solid shapes of the instant airfoils can be general prismatoids, such as, a sphere, a hemisphere, spherical triangle, spherical segment or sector, curved volume of a right cylinder, curved volume of a right cone, oblate spheroid, oblate hemispheroid, semi-hemispheroid, quai-hemnispheriod, prolate spheroid, prolate hemispheroid, frustum of right circular cone, solid lune, ellipsoid, and the like. Other unusual solid shapes can include an egg shape, a hemi-egg shape, a papaya shape, a hemi-papaya shape, a pear shape, a hemi-pear shape or almost any spheroidal or hemi-fruit shape. Still other shapes can include football or hemi-American-football shape.

Although solid general prismatoid shapes (unstremelined "blunt" shapes) such as spheroid shapes perform poorly in flight, most will not develop the required lift for sustained flight at any degree of spin. Lift can be imparted, however, to the solid general prismatoid shapes by modifying the solid shapes with an internal or external gel component having one or more substantially different gel rigidity regions. See FIG. 6 for examples of various profiles. The additional requirements for forming general prismatoids with one or more internal and/or external regions are: (1) the resulting bodies must have a sufficient volume of low gel rigidity region or regions for the bodies to exhibit a base diameter, D, (this is a measurable diameter advantageously of at least about 20% to 200% or more of the bodies' axes diameter and (2) a sufficient volume of high gel rigidity region or regions to allow a preselected volume of the bodies to support its own shape (i.e. moulded high gel rigidity shaped region) and exhibit a advantageously preselected amount of altitude, H, with a measurable height of about 20% or less to about 70% or more of the bodies' largest axes diameter. In order for the general prismatoids to have a base, the rigidity of the low gel rigidity region(s) should be at least about 50 gram Bloom or lower. A body formed in accordance with conditions (1) and (2) will exhibit a base when placed on a flat leveled surface of a preselected diameter. This base is defined as the surface area of contact of the body shape with the flat surface. For example, if a 6.5 cm diameter solid body shape is made from a uniformly high rigidity gel of say 80 gram Bloom or higher, the body will exhibit a base diameter of less than about 20% (less than about 1.3 cm) when place on a flat surface. Likewise, if a 6.5 cm diameter solid body shape is made from a uniformly low rigidity gel of say 20 gram Bloom or lower, the body will exhibit a base diameter greater than about 20% (greater than about 1.3 cm) when place on a flat surface. In both cases, the resulting low and high "uniform" gel solid body shapes will not have sufficient lift. If, however, one half of each of the low and high rigidity gel shapes are combined together, the resulting (non-uniform) solid body shape will exhibit a base diameter, D, greater than 20% of its axes diameter (due to the low rigidity half region ) and an altitude, H, of about 50% of its axes diameter or about 3.25 cm (due to the high rigidity half region). Such a non-uniform, unstremelined "blunt" shaped solid body will exhibit lift.

Various ways of making airfoils, such as forming a relatively low gel rigidity inner gel regions followed by a high gel rigidity outer (regions), are possible, as is the use of triple-layers (regions), etc. For example, the inner core of a general prismatoid shaped body can be made of urethane gel, the middle layer of silicone gel, and the outer layer of (SEBS) gel with varying rigidity regions.

Figure 3:
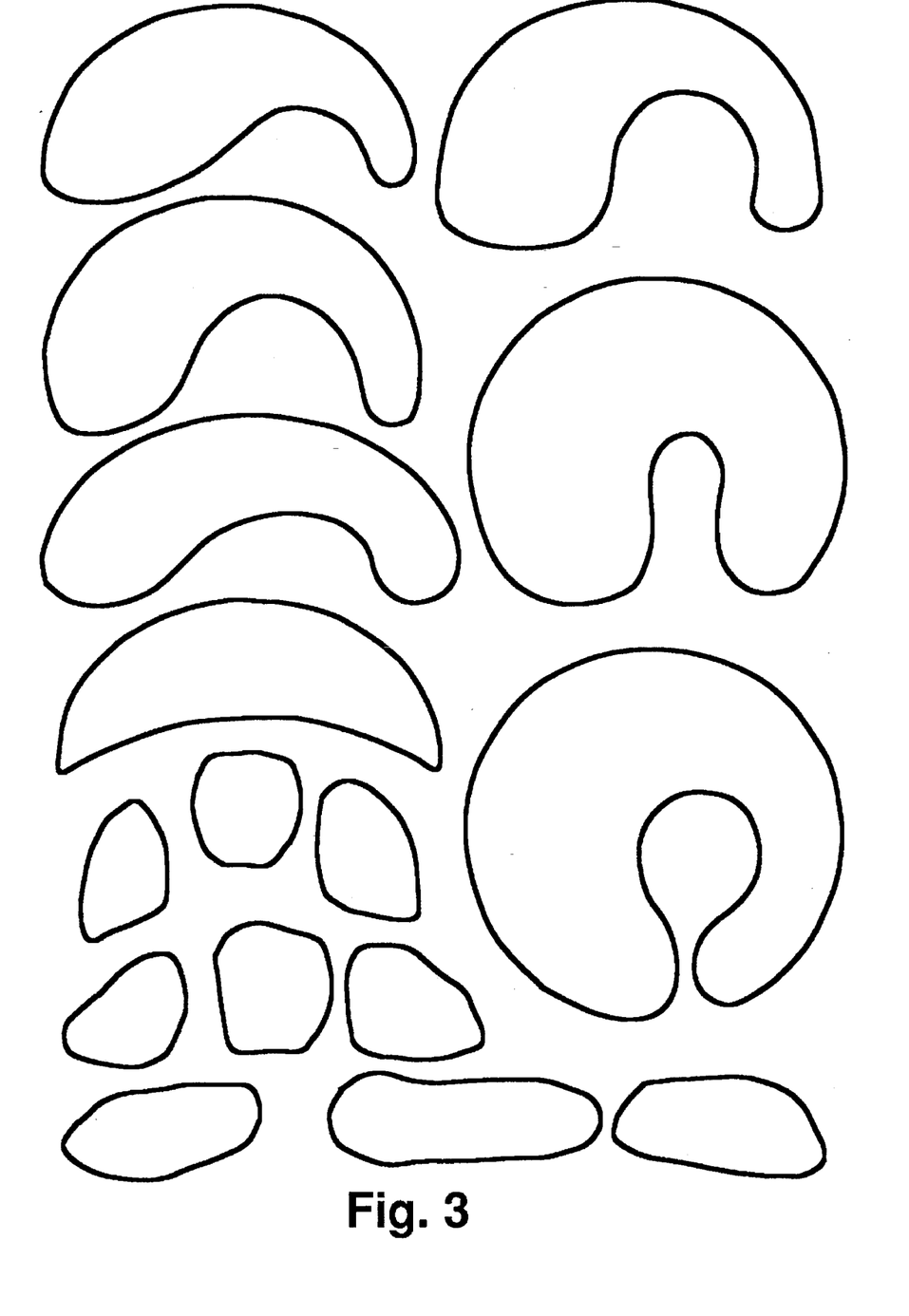
FIG. 3. Side view of various representative profile cross section imprint tracings of airfoils of the invention including an imprint of one of the airfoils at an elongation greater than 200%.
Figure 4:
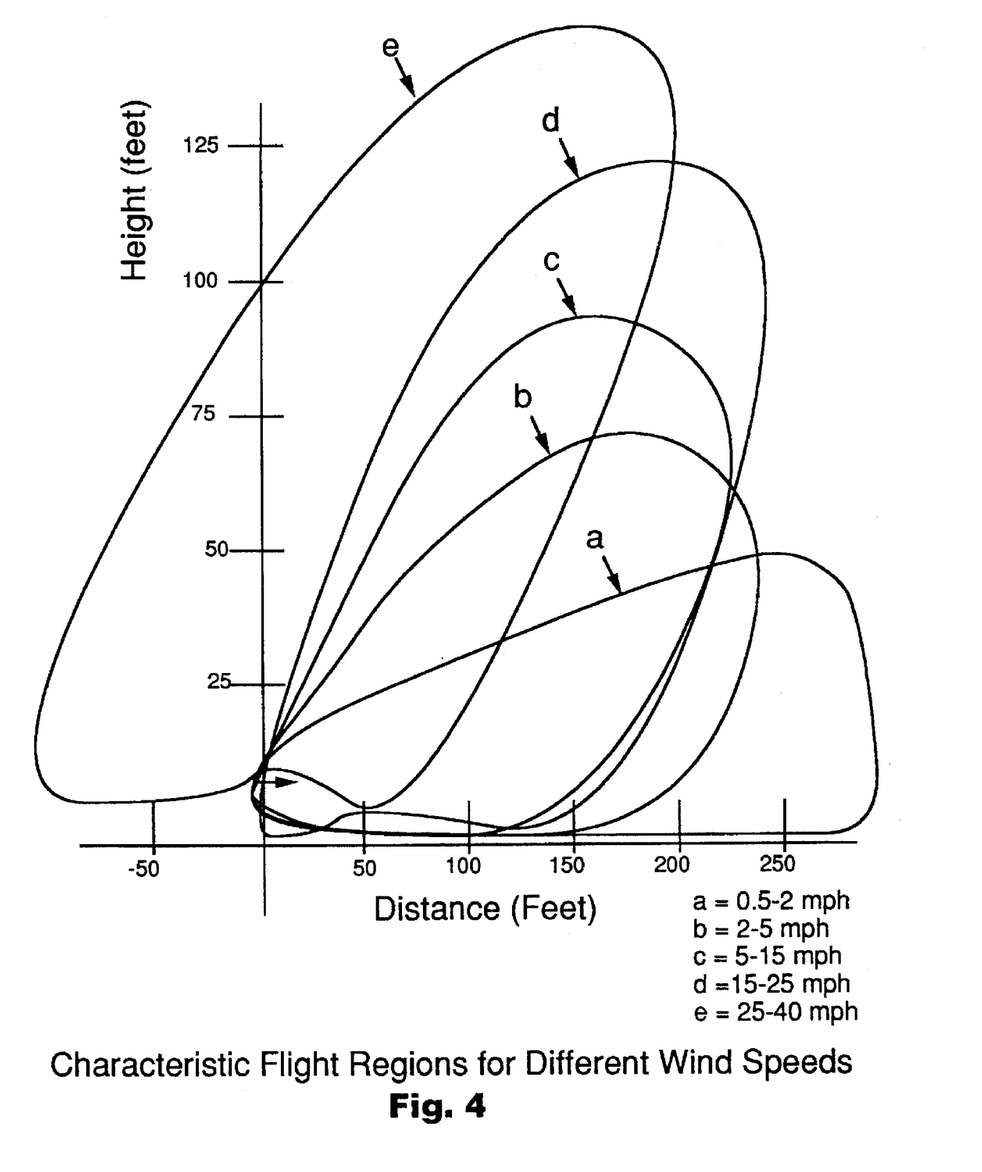
FIG. 4. Representative characteristic flight regions of airfoils under various wind conditions.
Figure 5:
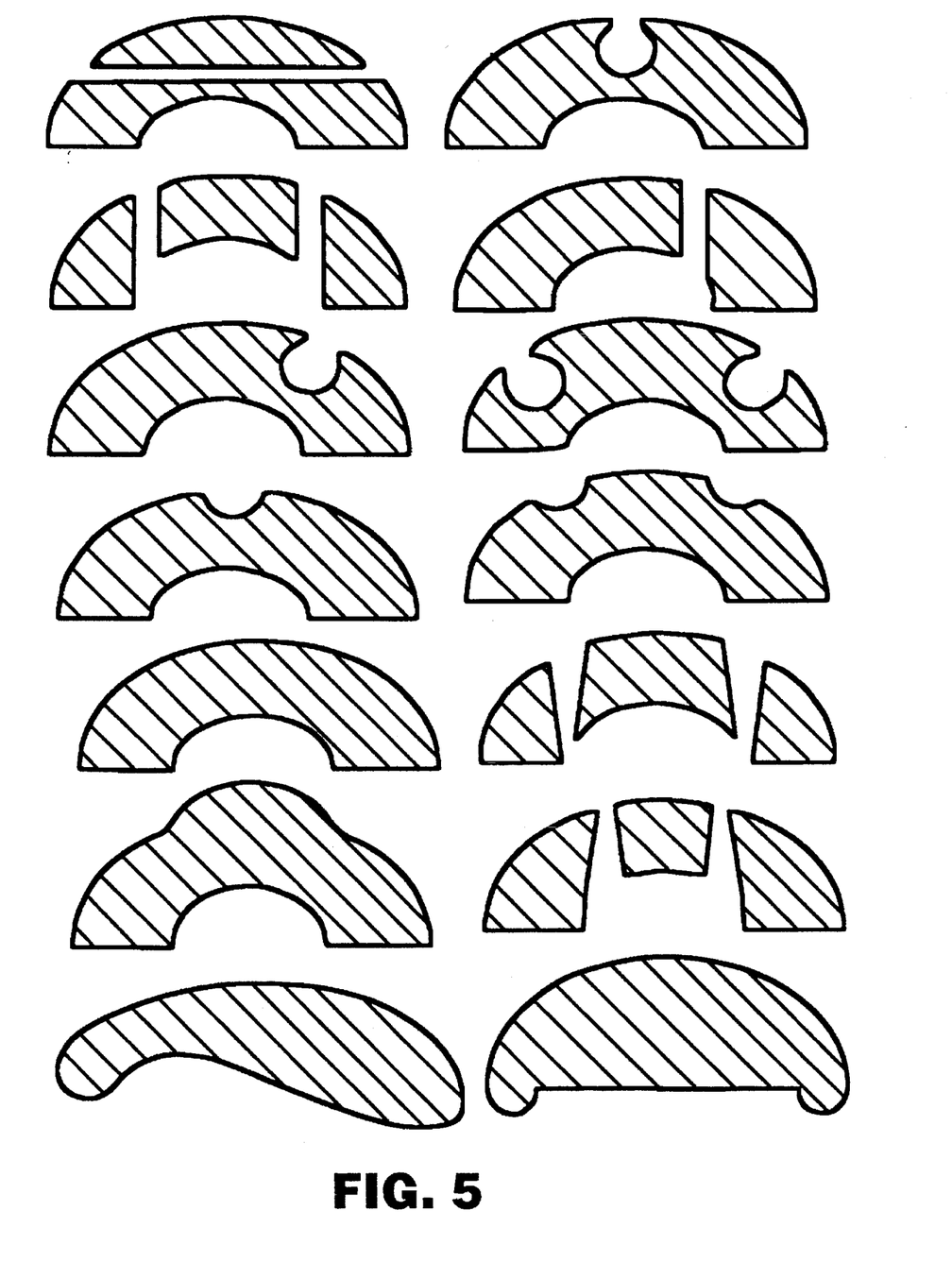
FIG. 5. Representative sectional views of hemispherical shaped blunt airfoils.
Figure 6:
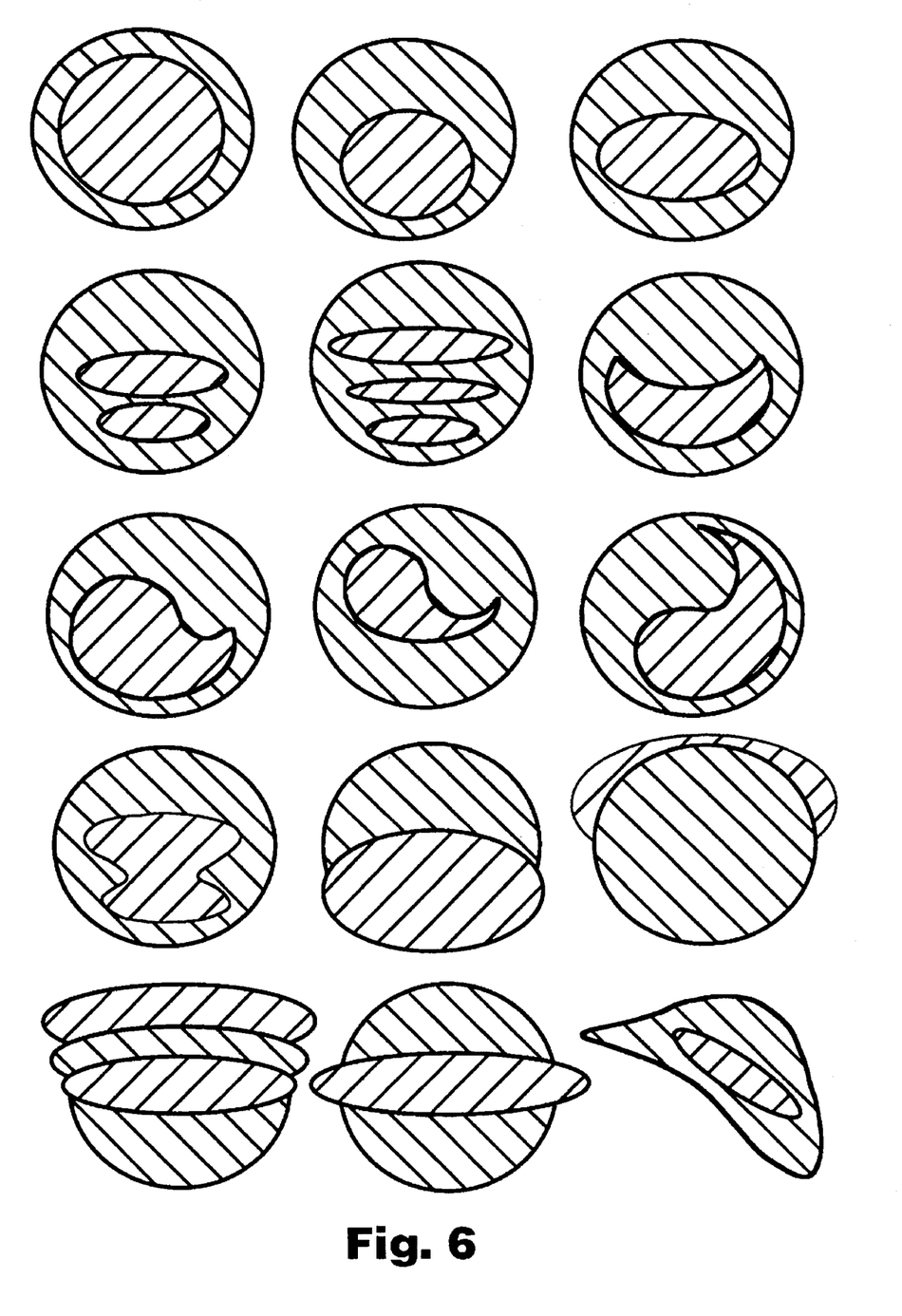
FIG. 6. Representative sectional views of various spheroid shaped airfoils with more than one gel regions.
Figure 7:
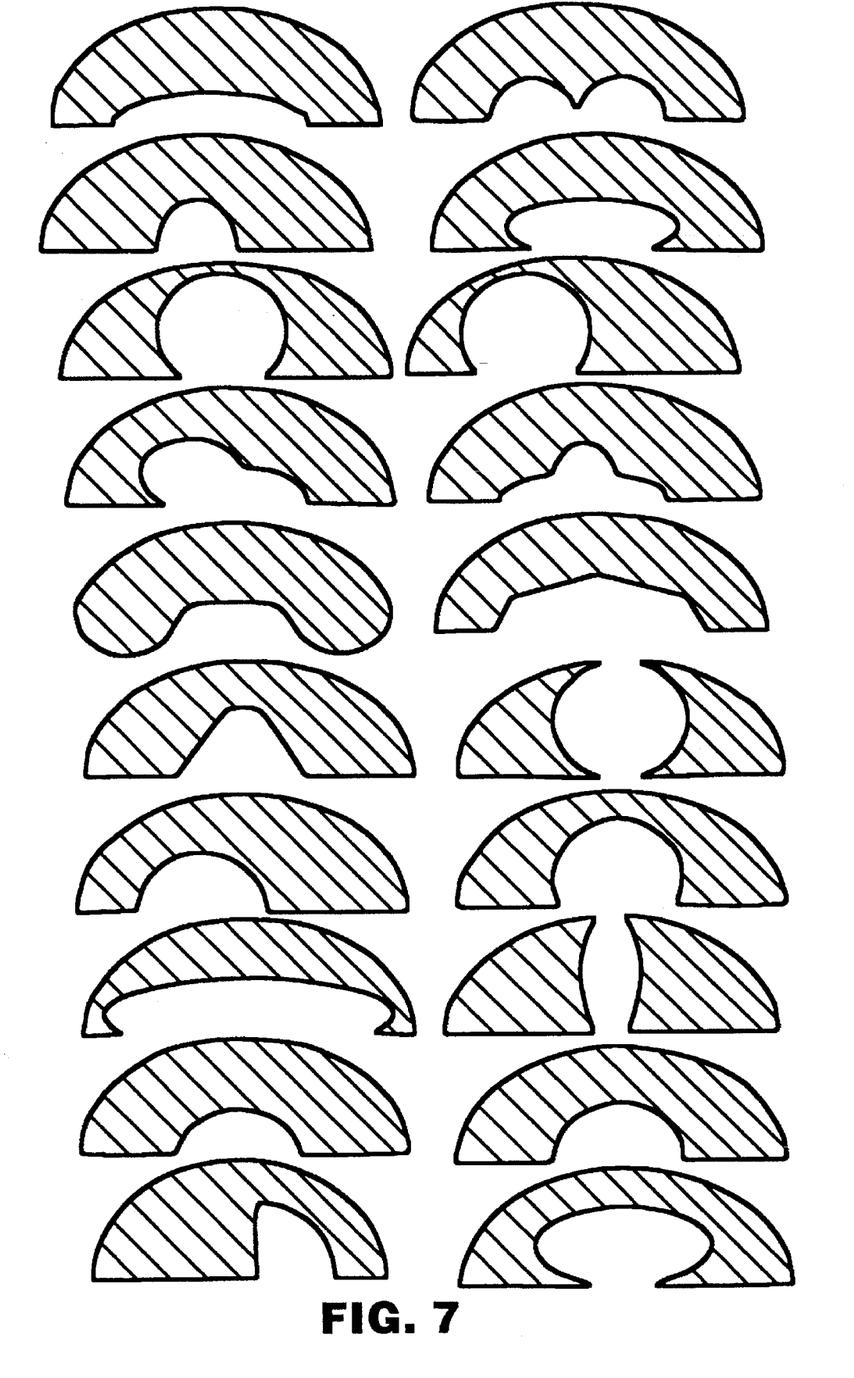
FIG. 7. More representative sectional views of hemispherical shaped blunt airfoils.
Figure 8:
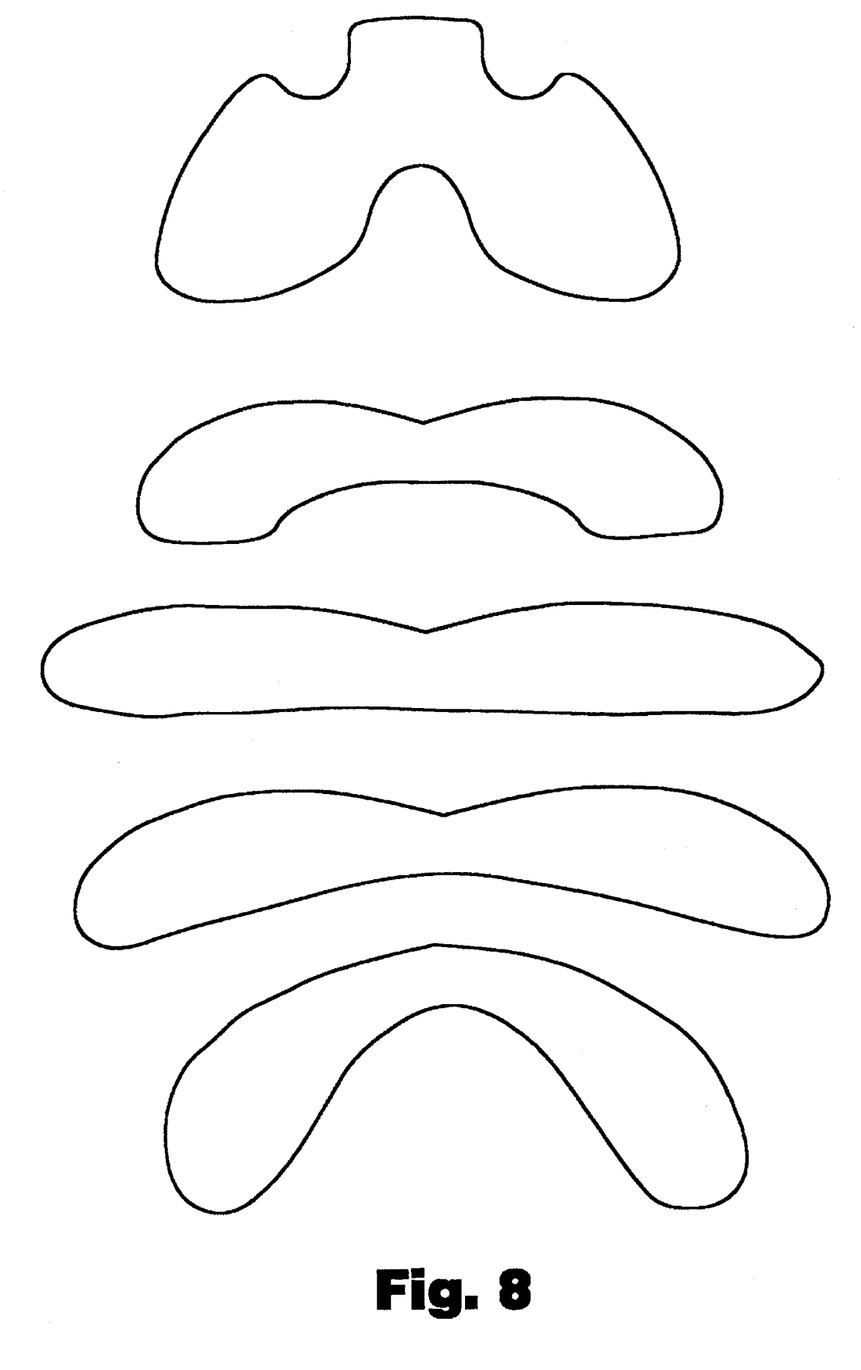
FIG. 8. Representative views of some more blunt and less blunt cross section imprint tracings of airfoils of the invention.
Figure 9:
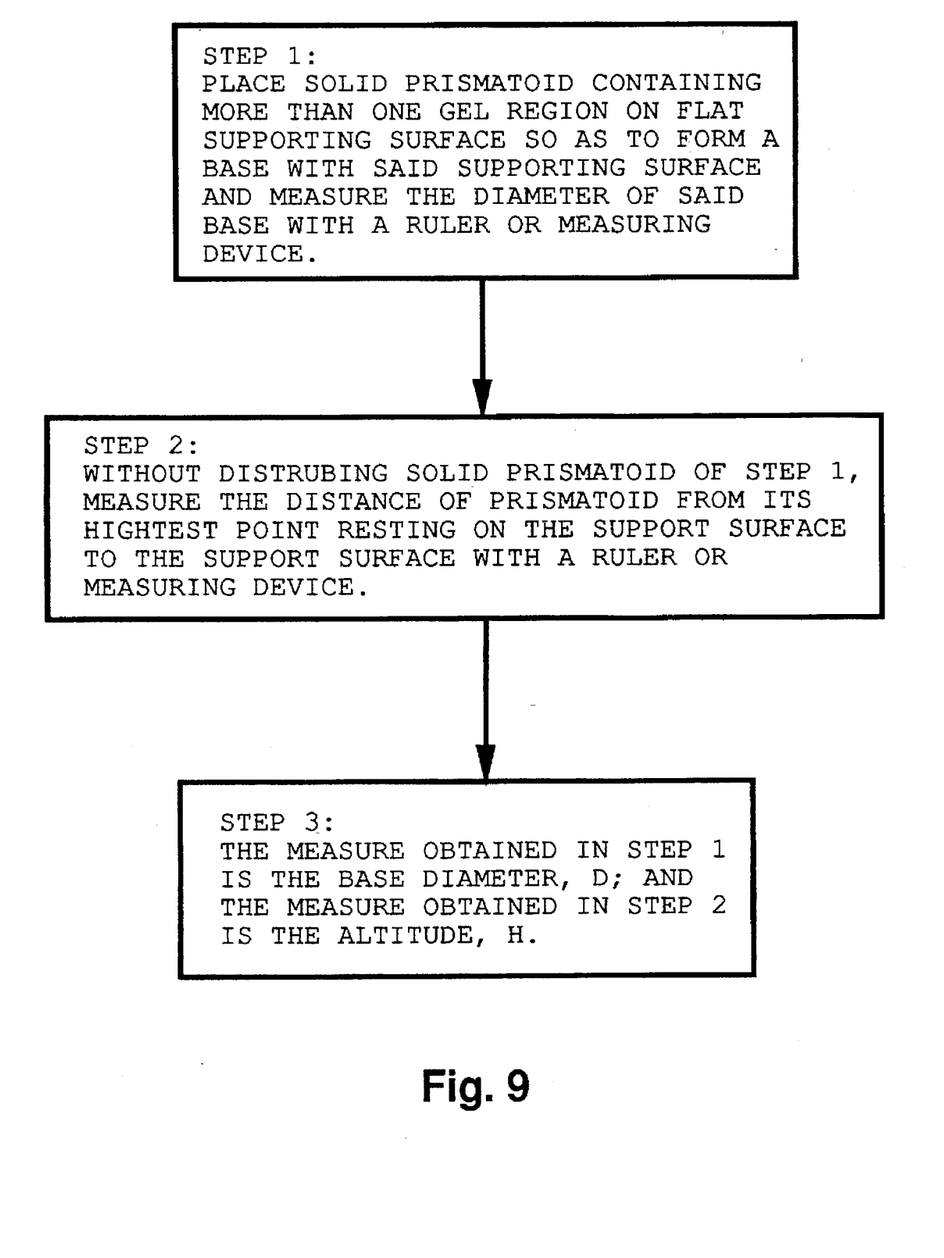
FIG. 9. Representative steps in measuring the base diameter D and altitude H.
Figure 10:
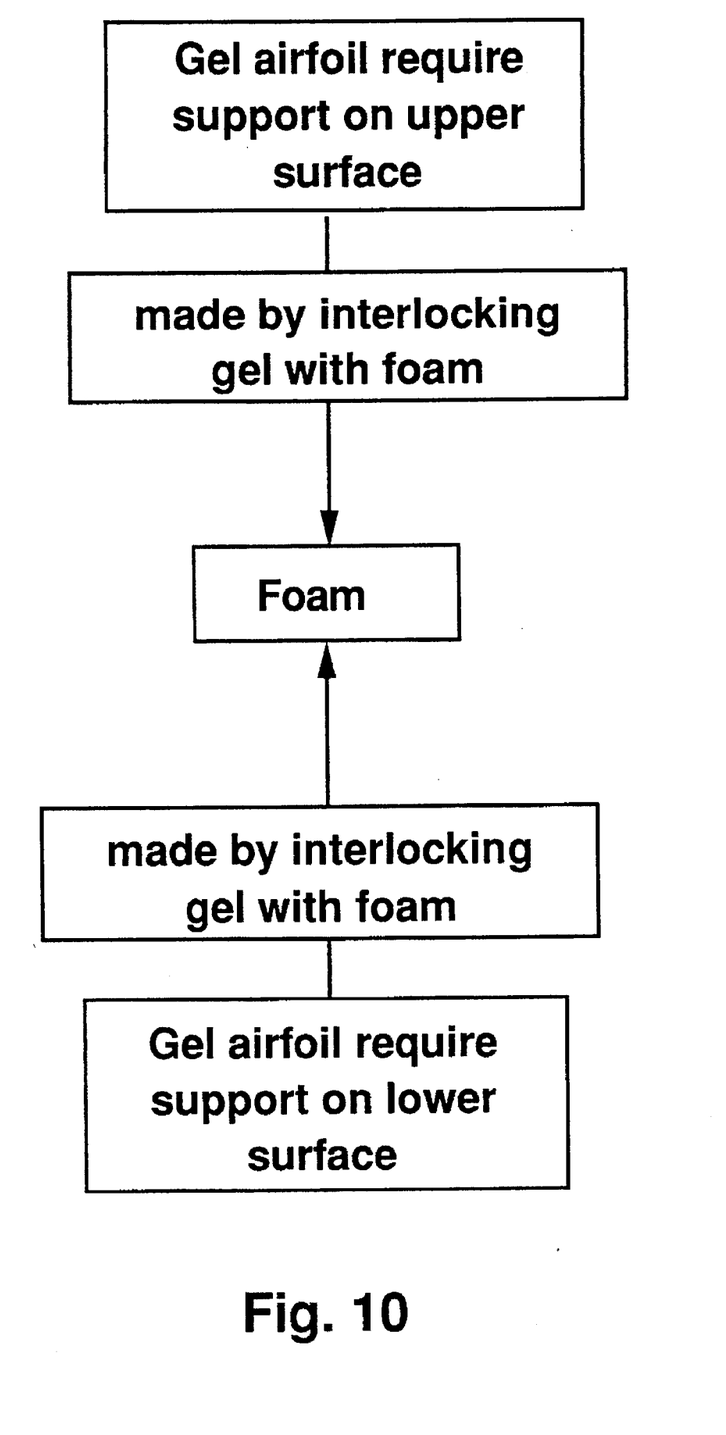
FIG. 10. Representative diagram of interlocking gel with foam.
Figure 11:
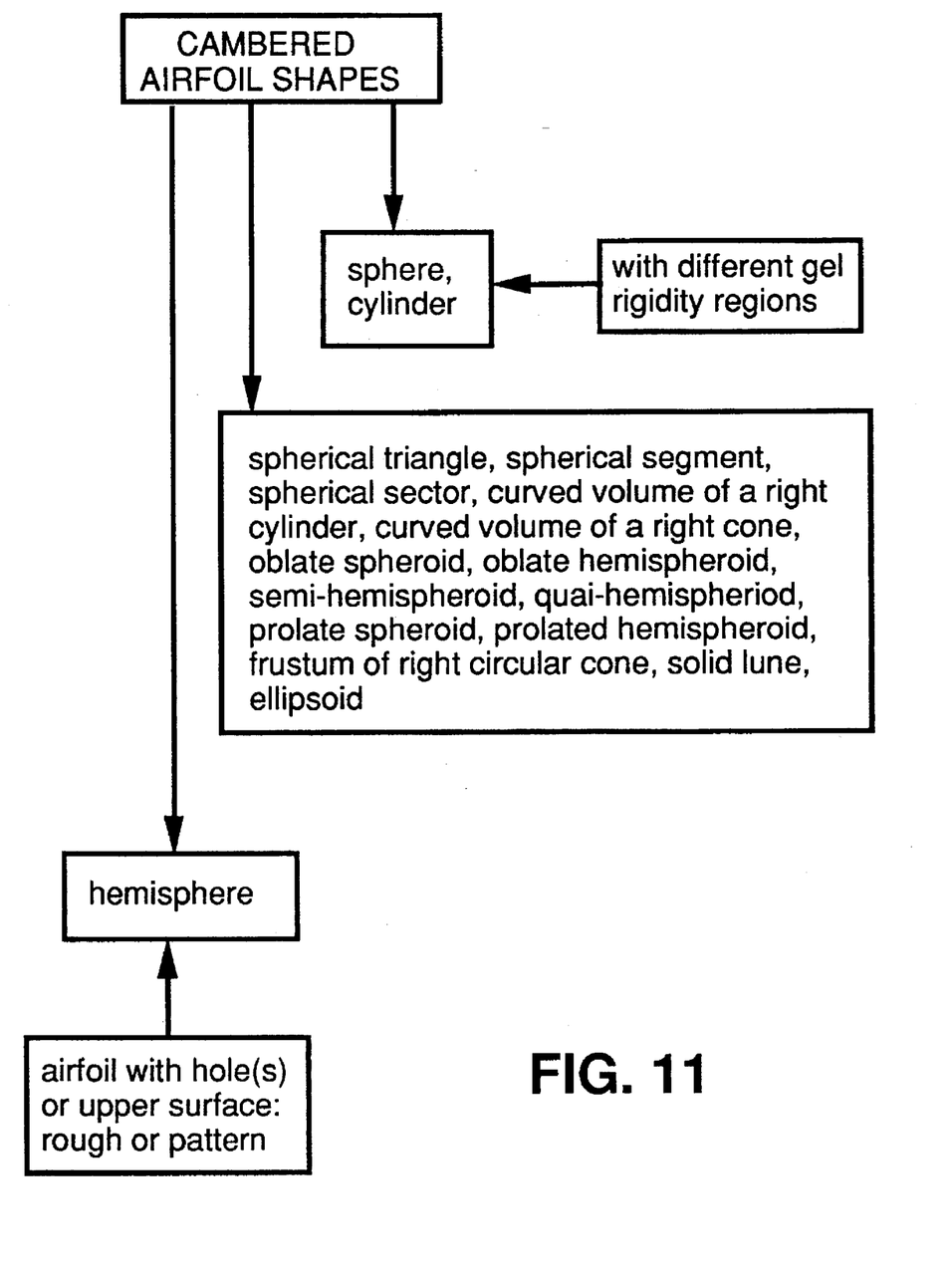
FIG. 11. Representative diagram comprising cambered airfoil shapes.
Figure 12:
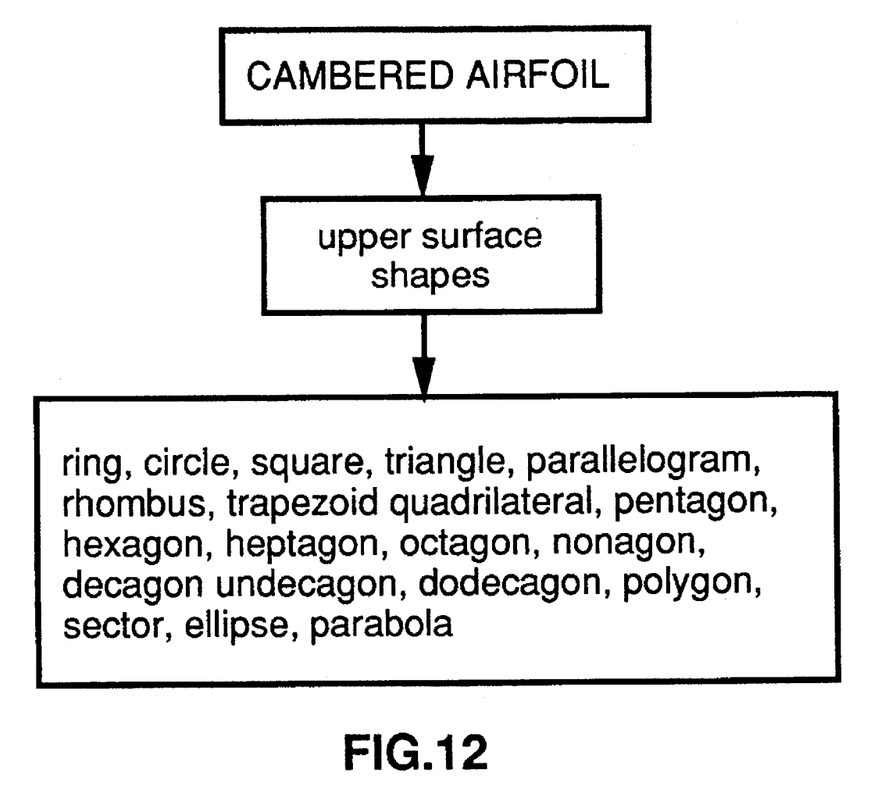
FIG. 12. Representative diagram comprising upper surface shapes of cambered airfoil.

The upper surface of airfoils of the invention can be smooth, patterned, rough, and the like. The upper surface can also contain one or more cavities, slots or holes completely through the airfoil (see FIGS. 3, 5 & 7). The lower surface can be curved to any desired degree (centered or off-centered), or it can contain one or more cavities (centered or off-centered) of any desired shape (see FIGS. 3, 5, 6, 7, & 8).

The airfoils of the invention can be launched by hand. Launching aids can also be used to grip the trailing edge of the airfoils such as a "V" shaped device to simulate the fingers and thumb. Normally, an airfoil of the invention is launched with a spin of the wrist. The spinning wrist action imparts rotation to the airfoil so as to elongate the airfoil as it leaves the hand. The elongated airfoil will continue to spin and maintain its flight path while at the same time reach a maximum elongation due to centrifugal force and then retract back to its original shape as the spin reach a maximum and slows to a stop. Elongations of the airfoils (as measured from leading edge to trailing edge) under flight conditions can reach 50% or more. Elongations of 100%, 200%, 300%, 400%, 500%, 600%, 700% and higher are possible under flight conditions. Airfoils of the invention can be designed to withstand elongations higher than 1,000% which can occur at extreme high spin speeds.

Airfoils of the invention can fly at rotational speeds, $R_s$, of less than about 10 rpm to greater than about 1,500 rpm.

The instant airfoils can be launched at speeds, $S_l$, less than about 5 mph to about 80 mph and higher.

Airfoils were tested in the laboratory and in the field using a few simple equipment. Airfoils were mounted on a variable spinning device. The rotational speeds were measured by using a GenRad 1546 digital stroboscope. Both natural and laboratory winds were measured using a Hall Airspeed Indicator. Laboratory winds (up to 55 mph) were generated using a Rotron Inc. Centrimax® model CXH33 Blower and wind tunnel assembly. Airfoil characteristics such as: angle of attack, geometrical profile, climb, drag, lift, Reynolds number, stall, rotational velocity, aspect ratio, stall, twist, pitch, sides angle, cord length, yaw angle, deformations, vibrations, air circulation and the like can be observed, measured and/or calculated under a variety of flight conditions.

Two Reynolds Numbers can be used to characterize the airfoils of the invention. These are: $R_{e1}$ and $R_{e2}$.

$$R_{e1}=\{[S_l-R_s(C_L/2)]C_o\}/V_{u,r}$$

and $$R_{e2}=\{[S_l+R_s(C_L/2)]C_o\}/V_{u,r}$$

where $V_{u,r}$=Viscosity/Density or approximate=0.15 cm²/second in air. $R_{e1}$ and d $R_{e2}$ can range from less than about 200 to about 100,000 or more. More suitably, $R_{e1}$, and $R_{e2}$ can range from less than about 5000 to about 50,000 and higher.

The instant airfoils can fly under almost any wind condition, almost no wind (0.01 m.p.h.), low wind (0.5 m.p.h.), light wind (0.6 m.p.h.), moderate light wind (15 m.p.h.), moderate wind (25 m.p.h.), high wind (35 m.p.h.) and even under wind gust conditions greater than 40 m.p.h.

The instant airfoils can be made from any gel material with suitable elastic properties. Gels described in patents and applications under "RELATED APPLICATIONS AND PATENTS", now sold under trademark Memory-Gel®, are especially advantageous and suitable for forming the airfoils of the invention. Gels less suitable and less advantageous for use include polymer gels, crosslinked polymer gels, and the like. These are found in U.S. Pat. Nos. 4,833,193; 4,709,982; 4,716,183; 4,497,538; 4,509,821; 4,351,913 and 4,432,607 Other less suitable gels include high strength silicone gels, urethane gels, water gels, and the like. Such gels are inherently weak and do not make good airfoils by themselves; they can not withstand the spinning forces. Weak gels can be enclosed by the stronger more advantageous gels described in the invention.

Gels especially suitable for use in making airfoils of the invention can be prepared by melt blending an admixture consisting essentially of: (A) 100 parts by weight of a high viscosity triblock copolymer of the general configuration poly(styrene-ethylene-butylene-styrene) where said triblock copolymer is characterized as having a Brookfield Viscosity of a 20 weight percent solids solution of said triblock copolymer in toluene at 25° C. of at least about 1,800 cps.

(B) from about 300 to about 1,600 parts by weight of an plasticizing oil.

The high viscosity triblock copolymers in (A) which are suitable for use in the present invention has a typical Brookfield Viscosity of a 20 weight percent solids solution in toluene at 25° C. of not less than about 1,800 cps, and preferably about 2,000 cps or higher. Typically, the Brookfield Viscosity values of (A) can range from about 1,800 cps to about 16,000 cps. Less typically, the Brookfield Viscosity values of (A) can range from about 1,800 cps to about 30,000 cps or higher.

The proportion of hydrocarbon plasticizing oil in (B) is more preferably from about 350 to about 1,600 parts per 100 parts of the triblock copolymer.

The high viscosity triblock copolymer of the invention can have a broad range of styrene end block to ethylene and butylene center block ratio of approximately about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C. Other less suitable (SEBS) polymers are Tuftec H 1051, H1041, H1052 and the like made by Asahi Chemical. These polymers can be combined with Kraton G as desired.

The styrene to ethylene and butylene weight ratios for these Shell designated polymers can have a low range of 20:80 or less. Although the typical ratio values for Kraton G 1651, 4600, and 4609 are approximately about 33:67 and for Kraton G 1855X approximately about 27:73, these ratios can vary broadly from the typical product specification values. For example, the styrene to ethylene and butylene weight ratio for Kraton G 1651, G4600, G 4609, and G 1855X can range from lower than about 20:80 to above about 40:60. More specifically, Kraton G 1651, Kraton G 1855X, Kraton G 4600, Kraton G 4609 Kraton G 1855X can have varying ratio values including 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 52:49 and the like. Other ratio values of less than 19:81 or higher than 52:49 are also possible. Broadly, the styrene end block to ethylene and butylene center block ratio of the triblock copolymers of the invention is about 20:80 to about 40:60, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers having ratios below 31:69 may be used, but they are less preferred due to their decrease in the desirable properties of the final gel composition.

Plasticizers particularly preferred for use in practicing the present invention are were known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available. Examples of representative commercially oils include Amoco® polybutenes, hydrogenated polybutenes and polybutenes with epoxide functionality at one end of the polybutene polymer: Example of such polybutenes include: L-14 (320 $M_n$), L-50 (420 $M_n$), L-100 (460 $M_n$), H-15 (560 $M_n$), H-25 (610 $M_n$), H-35 (660 $M_n$), H-50 (750 $M_n$), H-100 (920 $M_n$), H-300 (1290 $M_n$), L-14E (27–37 cst @100° F. Viscosity), L-300E (635–690 cst @210° F. Viscosity), Actipol E6 (365 $M_n$), E16 (973 $M_n$), E23 (1433 $M_n$) and the like. Example of various commercially oils include: ARCO Prime and Tufflo oils, other white mineral oils include: Bayol, Bernol, American, Blandol, Drakeol, Ervol, Gloria, Kaydol, Litetek, Marcol, Parol, Peneteck, Primol, Protol, Sontex, and the like.

The high viscosity triblock copolymer component by itself lacks the desired properties; whereas, when the triblock copolymer (having Brookfield Viscosities of a 20 weight percent solids solution in toluene at 25° C. of about 1,800 cps or higher and styrene to ethylene and butylene ratio preferably of the range contemplated in the instant invention) is combined with selected plasticizing oils with an average molecular weight preferably of about 200 to about 800 or more, as determined by ebulliscopic methods, wherein, for most purposes, the oil constitutes about 300 to about 1,600 parts and more preferably about 350 to about 1,600 parts by weight of the triblock copolymer, that an extremely soft and highly elastic material is obtained. This transformation of the triblock copolymer structure in heated oil resulting in a composition having a gel rigidity preferably of about 20 gram or lower to about 800 gram Bloom or more and substantially without oil bleedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter at 23° C.

In accordance with the practice of the present invention, the aforementioned molecular weight range plasticizing oils are most preferred. Generally, plasticizing oils with average molecular weights less than about 200 and greater than about 700 may also be used.

Minor amounts of other polymers and copolymers can be melt blended with the styrene-ethylene-butylene-styrene block copolymers mentioned above without substantially decreasing the desired properties. Such polymers may also be utilized in one or more regions of the airfoils of the invention; these include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, $(SB)_n$ styrene-butadiend and $(SEB)_n$, $(SEBS)_n$, $(SEP)_n$, $(SI)_n$ styrene-isoprene multi-arm, branched, and star shaped copolymers and the like. Still, other homopolymers can be utilized in minor amounts; these include: polystyrene, polybutylene, polyethylene and the like.

The proportion of hydrocarbon plasticizing oil in (B) is more preferably from about 350 to about 1,600 parts per 100 parts of the triblock copolymer.

The major triblock copolymers employed in the present invention have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. Most recent reviews of triblock copolymers are found in the "ENCYCLOPEDIA OF POLYMER SCIENCE AND ENGINEERING", Volume 2 and 5, 1987–1988; *"Thermoplastic elastomers"*, MODERN PLASTICS ENCYCLOPEDIA, 1989; and Walker, B. M., Ed., et al., HANDBOOK OF THERMOPLASTIC ELASTOMERS, Van Nostrand Reinhold Co., 2nd Edition, 1988. (incorporated herein by reference).

The composition of this invention can also contain useful amounts of conventionally employed additives such as stabilizers, antioxidants, antiblocking agents, colorants, fragrances, flame retardants, and the like to an extend not affecting or substantially decreasing the desired properties of the present invention.

Additives useful in the composition of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearyl-pentaerythritoldiproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl-benzene), 4,4"-methylenebis (2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, metallic pigments (aluminum and brass flakes), $TiO_2$, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite, talcum, and the like. The report of the committee on *Magnetic Materials*, Publication NMAB-426, National Academy Press (1985) is incorporated herein by reference.

The compositions of the present invention are prepared by blending together the components including other additives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amount of SEBS used. These components blend easily in the melt and a heated vessel equipped with a stirrer is all that is required. As an example, small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than about 10 rpm to about 40 rpm or higher.

The composition of the airfoils of the invention is excellent for cast molding and the molded products have various excellent characteristics which cannot be anticipated form hte properties of the raw components.

The basis of this invention resides in the fact that a high viscosity poly(styrene-ethylene-butylene-styrene) triblock copolymer when blended in the melt with an appropriate amount of plasticizing oil makes possible the attainment of compositions having a desirable combination of physical and mechanical properties, notably high elongation at break of at least 1,600%, ultimate tensile strength of about at least $8 \times 10^5$ dyne/$cm^2$, low elongation set at break of substantially not greater than about 2%, tear resistance of at least $5 \times 10^5$ dyne/$cm^2$, substantially about 100% snap back when extended to 1,200% elongation, and a gel rigidity of substantially not greater than about 800 gram Bloom.

More specifically, the composition utilized in the present invention exhibit one or more of the following properties. These are: (1) tensile strength of about $8 \times 10^5$ dyne/$cm^2$ to about $10^7$ dyne/$cm^2$; (2) elongation of about 1,600% to about 3,000% and higher; (3) elasticity modulus of about $10^4$ dyne/$cm^2$ to about $10^6$ dyne/$cm^2$; (4) shear modulus of about $10^4$ dyne/$cm^2$ to about $10^6$ dyne/$cm^2$ as measured with a 1,2, and 3 kilogram load at 23° C.; (5) gel rigidity of about 20 gram Bloom or lower to about 700 gram Bloom as measured by the gram weight required to depress a gel a distance of 4 mm with a piston having a cross-sectional area of 1 square cm at 23° C.; (6) tear propagation resistance of at least about $5 \times 10^5$ dyne/$cm^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C. It should be noted that when the ratio falls below 31:69, various properties such as elongation, tensile strength, tear resistance and the like can decrease while retaining other desired properties, such as gel rigidity, flexibility, elastic memory.

The instant airfoils molded from the compositions have various additional important advantages in that they do not crack, creep, tear, crack, or rupture in flextural, tension, compression, or other deforming conditions of normal use; but rather the molded airfoils made from the instant composition possess the intrinsic properties of elastic memory enabling the airfoils to recover and retain its original molded shape after many extreme deformation cycles. In applications where low rigidity, high elongation, good compression set and excellent tensile strength are important, the instant compositions would be preferred.

The composition can also be formed into shapes for use as optical lenses. The optical lenses may have two or more opposite regular surfaces either both curved or one curved and the other plane. Such lenses may be used either singly or combined in an optical instrument or in the hand for forming an image by focusing rays of light. Example of lens shapes include plano-convex, bi-convex. converging meniscus, plano-concave, bi-concave, diverging meniscous, cylindrical, and spherical.

The composition of the invention is extremely versatile; it can be casted, molded, or extruded to make the airfoils of the invention.

The invention is further illustrated by means of the following illustrative embodiments, which are given for purpose of illustration only and are not meant to limit the invention to the particular components and amounts disclosed.

EXAMPLE I

One hundred parts by weight of a high viscosity poly (styrene-ethylene-butylene-styrene) triblock copolymer (Shell Kraton G 1651 ) with 0.1 parts by weight of a stabilizer (Irrganox 1010) was melt blended with various quantities of a naphthenic oil (ARCO Tufflo 6024). Samples having the dimensions of 5 cm×5 cm×3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table I below.

TABLE I

| Oil per 100 parts of Triblock copolymer | Gel Rigidity, gram Bloom |
| --- | --- |
| 360 | 500 |
| 463 | 348 |
| 520 | 280 |
| 615 | 240 |
| 635 | 220 |
| 710 | 172 |
| 838 | 135 |
| 1,587 | 54 |

TABLE II

| Experiment | 400% elongation Rotation Speed rpm | Gel Rigidity, gram Bloom |
| --- | --- | --- |
| 1 | 732 | 51 |
| 2 | 805 | 75 |
| 3 | 929 | 105 |
| 4 | 941 | 109 |
| 5 | 835 | 82.5 |
| 6 | 989 | 113 |
| 7 | 1095 | 140 |

EXAMPLE II

Two plano-convex lenses having a rigidity of 105 are joined at their bases to form a sphere. The resultant sphere is thrown against a hard smooth glass door and upon impact is deformed into the shape of a pancake; upon recovery back to the original shape of a sphere, it slowly roll down the surface of the door under the force of gravity. The lenses are then joined at their base with only half of the total base surface areas overlapping; the joined lenses are thrown against a hard smooth glass door and upon recovery the lenses in union rolls down the surface of the door showing cam rolling action.

Such a plano-convex lens can serve as a symmetrical airfoil provided it is detackfied with talcum or other detackfying agents. Otherwise if thrown in its tacky state, chances are it will hit your foot. A stretchey, gooey, soft and sticky toy in the shape of a plano-convex lens (trademarked Glueball®) has been marketed since 1983 by Applied Elastomerics, Inc. As one writer have said of this toy and other toys like it:

"People have been known to stand in front of a large wall, and from arm's length, rear back, let fly, and miss entirely. The wall." Although it may work poorly as an airfoil, a slight difficulty with using one-half of a detackfied Glueball® or plano-convex lens without its lower surface curved to any degree is that it will require a much higher spin when launching such an airfoil in order to obtain the desired flight performance. The higher spin means a greater centrifugal force is needed which results often times in tearing of the underside of the airfoil only after a few throws. Moreover, the greater spin required to launch the airfoil is beyond the normal endurance of the average adult human hand and wrist.

The discovery of the present invention was made by a chance accident. While examining a newly made Glueball®, the inventor inadvertently dropped one of the hemisphere on some small pumice rocks near his foot and on picking it up, several small rocks were tenaciously attached to the hemisphere. The rocks attached to the hemisphere would not come off no matter how hard the hemisphere was shooked. The inventor next tried to sling the rocks off; it also did not work. An attempt to sling the hemisphere as hard as possible resulted in breaking a small piece of the hemisphere off thereby unintentionally releasing the hemisphere-rocks spinning into the air. The inventor observed that all the rocks separated upon release; but the hemisphere spinning with the curved side facing down did not follow the normal path of a falling projectile. Rather, it dipped drastically in midcourse and plunged into the ground picking up a hand-full of more pumice rocks. Talcum was applied to the other hemisphere; upon launched in the same manner with its curved side up, the spinning hemisphere took on a noticeably deformed shape and lifted-up into the air, maintaining a sustained flight for quite some distance. Since that day, the inventor has worked to improve on the hemisphere airfoil to solve the problem of tearing and decreasing the spin rate required for use by small and younger hands. Table II gives results of spin speed (rpm) as a function of rigidity at an observed elongation of approximate 400%.

EXAMPLE III

Airfoil designs which require support and/or stability on its upper or lower surfaces can be made by interlocking the gel with a foam. Such a foam is SCOTFOAM® 1/32" to 1/8" thick sheet material with 5, 10, 15, 20, 25, 30, 35, 40, 45, 50, 60, 70, 80, 90, 100, and 200 ppi.

While preferred components and formulation ranges have been disclosed herein. persons of skill in the art can extend these ranges using appropriate material according to the principles discussed herein. All such variations and deviations which rely on the teachings through which the present invention has advanced the art are considered to be within the spirit and scope of the present invention.

What I claim is:

1. An aerodynamic toy comprising: an ultra-elastic gel airfoil having a profile defining a camber, said airfoil having an upper surface and a lower surface, said airfoil having one or more holes; and said airfoil capable of exhibiting an elongation of at least 50% caused by a centrifugal force of rotation during flight.

2. An aerodynamic toy comprising: an ultra-elastic gel airfoil having a profile defining a camber, said airfoil having an upper surface and a lower surface, said airfoil having one or more cavities; and said airfoil capable of exhibiting an elongation of at least 50% caused by a centrifugal force of rotation.

3. An aerodynamic toy of claim 1, wherein said gel airfoil having one or more different gel rigidity regions.

4. An aerodynamic toy of claim 1, wherein said gel airfoil having a first and a second gel regions, said first gel region having a gel rigidity of about 50 gram to about 800 gram Bloom, and said second gel region having a gel rigidity of about 2 gram to about 40 gram Bloom.

5. An aerodynamic toy of claim 2, wherein said ultra-elastic gel airfoil having at least one external region formed from at least one gel having a gel rigidity of about 50 gram to about 800 gram Bloom, said airfoil having at least one internal region formed from at least one gel having a gel rigidity of about 5 to 80 gram Bloom and said airfoil capable of forming a substantially streamlined shape when extended.

6. An aerodynamic toy according to claim 1, wherein said gel airfoil having a shape of substantially a circle, a square, a triangle, a parallelogram, a rhombus, a trapezoid, a quadrilateral, a pentagon, a hexagon, a heptagon, a octagon, a nonagon, a decagon, a undecagon, a dodecagon, a polygon, a sector, an ellipse, or a parabola.

7. An aerodynamic toy comprising: an ultra-elastic gel airfoil having a profile defining a camber, said gel airfoil having one or more of a first internal and a second external gel rigidity regions, said first and second gel rigidity regions having different gel rigidities, and said gel airfoil having one or more axes, a base contact diameter, D, and a altitude, H, said D having a value at least about 20% to about 200% of one of its axes, and said altitude having a value of about 20% to 80% of one of its axes; wherein the values of D and H being measured when said gel airfoil is supported on a support surface.

8. An aerodynamic toy of claim 7, wherein said airfoil is substantially an ellipsoid, a spheroid, an oblate spheroid, or a prolate spheroid.

9. An aerodynamic toy comprising: an ultra-elastic gel airfoil having a profile defining a camber, said airfoil having one or more cavities; and said airfoil capable of exhibiting an elongation of at least 50% caused by a centrifugal force of rotation during flight.

10. An aerodynamic toy comprising: an ultra-elastic gel airfoil having a profile defining a camber, said airfoil having one or more slots; and said airfoil capable of exhibiting an elongation of at least 50% caused by a centrifugal force of rotation during flight.

11. An aerodynamic toy comprising: an ultra-elastic gel airfoil having a profile defining a camber, said airfoil having one or more holes and cavities; and said airfoil capable of exhibiting an elongation of at least 50% caused by a centrifugal force of rotation during flight.

12. An aerodynamic toy comprising: an ultra-elastic gel airfoil having a profile defining a camber, said airfoil having one or more holes and slots; and said airfoil capable of exhibiting an elongation of at least 50% caused by a centrifugal force of rotation during flight.

13. An aerodynamic toy of claim 1, 2 or 11 wherein said airfoil is made from a gel having a gel rigidity of about 2 gram to about 800 gram Bloom.

14. An aerodynamic toy comprising: an ultra-elastic gel airfoil having a profile defining a camber, said airfoil having one or more holes, cavities, or slots; and airfoil having a rough or pattern surface, and said airfoil capable of exhibiting an elongation of at least 50% caused by a centrifugal force of rotation during flight.

15. An aerodynamic toy of claim 1, 9 or 14 wherein said airfoil is made from a gel having a rigidity of about 50 gram to about 800 gram Bloom.

16. An aerodynamic toy comprising: an ultra-elastic gel airfoil having a profile defining a camber, said airfoil having a first internal and a second external gel rigidity regions, said first and second gel rigidity regions having different gel rigidities, and said gel airfoil having one or more axes, said airfoil having a base contact diameter, D, and a altitude, H, said D having a value at least about 20% to about 200% of one of its axes, and said altitude having a value of about 20% to 80% of one of its axes; wherein the values of D and H being measured when said gel airfoil is supported on a support surface.

17. An aerodynamic toy of claim 16 or 14 wherein said gel airfoil having a rough or pattern surface.

18. An aerodynamic toy of claim 1 wherein said upper surface or lower surface of said gel airfoil is interlocked with a foam material.

19. An aerodynamic toy of claim 1, 9, 10, 11, or 12 wherein said gel airfoil having a cord line length of about 3 cm to about 30 cm measured at an elongation of at least 50%.

20. An aerodynamic toy of claim 1, 2, 10, 11, or 12 wherein said gel airfoil having at least one of a upper surface and a lower surface and said upper surface or said lower surface having a pattern or is rough.

21. An aerodynamic toy comprising an ultra-elastic gel airfoil having a profile defining a camber, said airfoil having one or more holes, cavities and slots; and said airfoil capable of exhibiting an elongation of at least 50% caused by a centrifugal force of rotation during flight.

22. An aerodynamic toy of claim 1, 2, 7, 16, or 14 wherein said gel airfoil having substantially a general prismatoid shape.

23. An aerodynamic toy of claim 1, 9, 10, 11, or 12 wherein said gel airfoil having a cord line length of about 3 cm to about 30 cm, a maximum thickness of about 1 cm to about 7 cm, and a value of $C_o$ of about 2 cm to about 20 cm, as measured at an elongation of at least 50%.

24. An aerodynamic toy of claim 7, or 16 wherein said external region formed from at least one gel having a gel rigidity of about 50 gram to about 800 gram Bloom, said internal region formed from at least one gel having a gel rigidity of about 5 to 80 gram Bloom and said body capable of forming a substantially streamlined airfoil when extended.

25. An aerodynamic toy of claim 7 or 16 wherein at least one of said external region formed from a gel having a gel rigidity of about 50 gram to about 800 gram Bloom, and at least one of said internal region formed from a gel having a gel rigidity of about 5 to 80 gram Bloom.

26. An aerodynamic toy comprising: an ultra-elastic gel airfoil having a profile defining a camber, said airfoil having one or more holes and slots; and said airfoil capable of exhibiting an elongation of at least 50% caused by a centrifugal force of rotation during flight.

27. An aerodynamic toy of claim 1, 9, 10, 11, 12, or 26 wherein said gel airfoil having two or more holes and one or more cavities, two or more holes and one or more slots, one or more cavities and slots, or two or more holes, cavities, and slots.

28. A method of launching an aerodynamic toy in the shape of an airfoil having a upper surface, a lower surface, one or more holes, one or more cavities, one or more slots; or one or more of a first internal and a second external regions, said upper and lower surfaces converging to form an edge, which comprises:

(a) gripping the edge of an airfoil made from an ultra-soft and ultra-elastic gel between the forefinger and the thumb of one hand, and (b) elongating said airfoil by launching the airfoil with sufficient rotational velocity so as to elongate said airfoil at least 50% or greater due to the centrifugal force of rotation.

* * * * *